United States Patent [19]

Raveed

[11] 4,051,755
[45] Oct. 4, 1977

[54] ULTRAMICROTOME AND ATTACHMENT THEREFORE

[75] Inventor: Dan Raveed, Xenia, Ohio

[73] Assignee: Charles F. Kettering Foundation, Dayton, Ohio

[21] Appl. No.: 730,450

[22] Filed: Oct. 7, 1976

[51] Int. Cl.² .............................................. G01N 1/06
[52] U.S. Cl. ...................................... 83/167; 83/168; 83/414; 83/701; 83/915.5
[58] Field of Search ................. 83/167, 168, 169, 414, 83/701, 915.5

[56] References Cited

U.S. PATENT DOCUMENTS 3,504,335  11/1970  Sitte .................................. 83/915.5 X Primary Examiner—J. M. Meister
Attorney, Agent, or Firm—Biebel, French & Nauman

[57] ABSTRACT

An ultramicrotome has a chuck for holding a specimen block and a stationary knife assembly. A radioactive means is mounted on the ultramicrotome for discharging static electric charge on the chuck, the specimen, and the knife assembly.

12 Claims, 5 Drawing Figures

ULTRAMICROTOME AND ATTACHMENT THEREFORE

BACKGROUND OF THE INVENTION

The present invention relates to ultramicrotomy and, more particulary, to an ultramicrotome for improved sectioning of specimens. An ultramicrotome is a device for sectioning thin slices of specimen material for electron microscopic analysis. Typically, organic specimen material is embedded in a block of epoxy after being heavily stained with uranium and osmium. Thin slices, or sections, on the order of 1000 Angstrums in thickness, are then made of the specimen block using the ultramicrotome. Production of such thin sections with the ultramicrotome remains somewhat of an art and requires a high degree of skill. This sectioning operation typically is viewed by the ultramicrotome operator through a microscope mounted on the device.

The ultramicrotome typically includes a chuck for holding the specimen block. Cutting of the block is accomplished with a diamond knife which is held stationary as the specimen block is moved into cutting contact. Glass knives may be used for only a few sections before they lose their sharpness and must be discarded; for this reason glass knives are generally used only by students. Diamond edge knives, while expensive, maintain a sharp edge during extended periods of use and are, therefore, preferred for most applications. The diamond knife is held by an assembly includinga knife boat which holds a quantity of fluid. The diamond knife extends across one edge of the knife boat and the boat may be filled with water so that the water extends just up to the cutting edge of the knife.

The specimen chuck is typically fastened to the end of a cantilever arm connected to a linkage which may be driven either by a hand crank or by a small motor. The linkage is arranged such that the specimen block is moved downward and into contact with the knife edge. After a section is cut, specimen block is moved laterally and returned to a position above the knife edge in preparation for the next downward cutting stroke. Between each downward cutting stroke, the specimen block and chuck assembly is advanced a predetermined distance toward the knife such that sections of the desired thickness are cut. This advancement arrangement may be either a mechanical system in which a threaded rod connected to the cantilever arm is rotated through a predetermined angle, or a thermal system in which the temperature of a rod having known thermal expansion characteristics is altered slightly during each cutting stroke.

The thin sections which are produced by the ultramicrotome are floated onto the surface of the fluid in the knife boat as they are cut in order to prevent them from being crumpled or otherwise destroyed. It is therefore important that the fluid surface extend up to the cutting edge of the diamond knife. It is very important, however, that this fluid at no time migrate over the knife edge surface and onto the outer edge of the knife. If this occurs, the specimen block will be wetted during each cutting stroke and successful sectioning will become impossible.

The problem of wetting the outer surface of a diamond knife is relatively common. In the operating instruction manual for the SORVALL MT2-B "Porter Blum" ultramicrotome, the following comment is made:

"Sometimes one encounters a situation in which the fluid in the trough seems to 'jump' onto the block face as it passes the knife, making sectioning difficult, if not impossible. This may be due to a drop of fluid on the vertical face of the knife (toward the specimen), and in this case can be cured by removing this fluid with a piece of the lens tissue. If this doesn't work, lowering the level of the fluid in the trough may help. If this makes it difficult to see the sections as they are cut, move the microscope forward and the lamp closer to the panel of the microtome and tip the microscope to recover the correct image of the knife and sections. It may even be necessary to sacrifice the image of the section nearest the knife edge to get the fluid level low enough to prevent wetting of the block face."

It is seen, therefore, that a need exists for an improved ultramicrotome device in which the migration of the fluid over the edge of the knife is eliminated, thereby permitting move uniform sectioning.

SUMMARY OF THE INVENTION

An ultramicrotome includes a chuck means holding a specimen and a stationary knife assembly for cutting the specimen. The knife assembly includes a knife boat which holds a quantity of fluid and a very sharp diamond edged knife defining one side of the knife boat. Means are provided for moving the chuck means into contact with the knife to cut sections from the specimen. Radioactive means are mounted on the chuck for discharging static electric charge on the chuck means and the knife assembly, whereby static charge forces are eliminated and the fluid is prevented from migrating over the knife as the chuck means approaches it.

The radioactive means may include an adapter which is mounted on the chuck means and an annular mount which is attached to the adapter ring upon which radioactive material is mounted. Theradioactive material may comprise polonium 210, providing a source of alpha rays.

Accordingly, it is an object of the present invention to provide an ultramicrotome in which migration of fluid in the knife boat over the cutting edge of the knife is prevented; to provide such an ultramicrotome including a source of radiation adjacent the specimen chuck and knife; and to provide such an ultramicrotome in which the source of radiation may be quickly and economically replaced.

Other objects and advantages of the invention will be apparent from the following description, the accompanying drawings and the appended claims.

DETAILED DESCRIPTION OF THE PREFERRED EMBODIMENT

Figure 1:
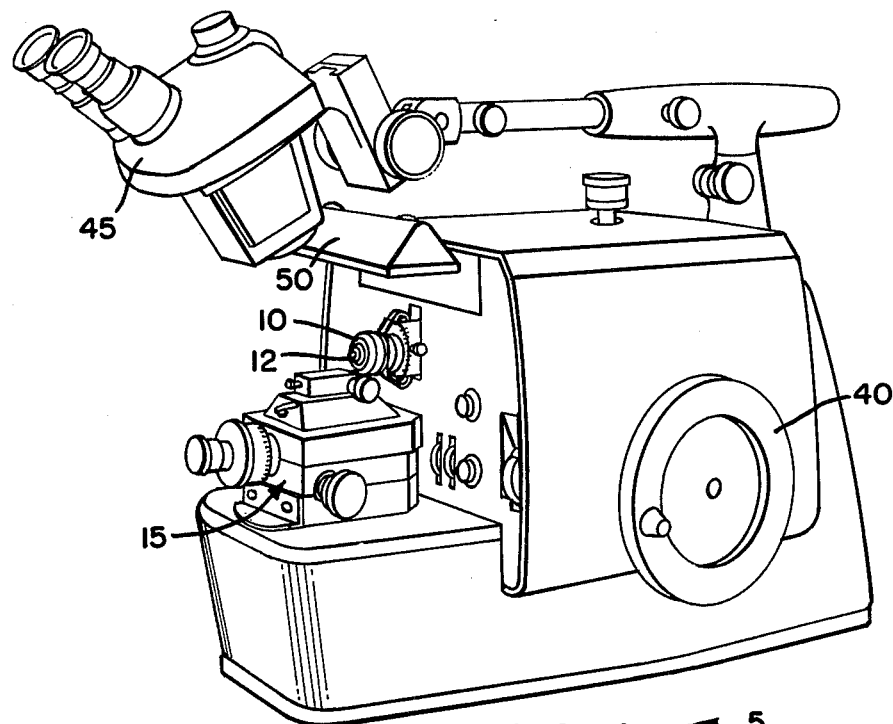
FIG. 1 is a perspective view of an ultramicrotome.
Figure 2:
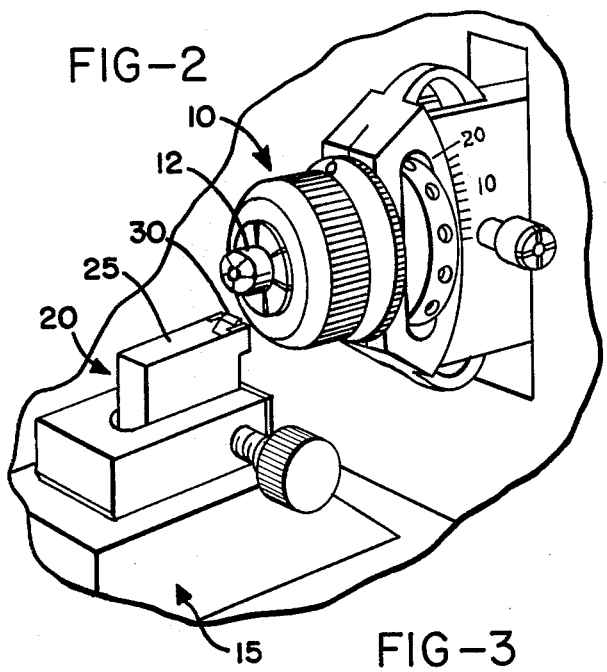
FIG. 2 is an enlarged perspective view of a portion of the ultamicrotome of FIG. 1, showing a knife assembly and specimen block.
Figure 3:
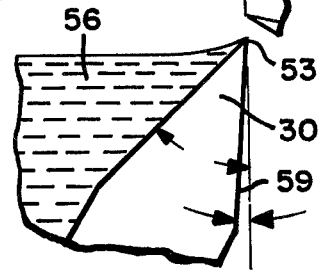
FIG. 3 is an enlarged and somewhat diagrammatic view, illustrating sectioning with an ultramicrotome.

Referring to FIGS. 1, 2, and 3, an ultramicrotome of the type used with the present invention is shown. A chuck means 10 is provided for holding a specimen block 12 which is to be sectioned. Knife stage assembly 15 is provided to position and secure a stationary knife assembly means 20 (FIG. 2). Stationary knife assembly means 20 includes a knife boat 25 for holdng a quantity of fluid and a diamond knife 30 which is held by the knife boat. Diamond knife 30 defines one side of the knife boat 25. Means for moving chuck means 10 and specimen block 12 may include an electric motor (not shown) and a hand wheel 40, which may be used as an alternative to the motor. Rotation of hand wheel 40 causes downward movement of specimen block 12 into cutting contact with knife edge 30. Continued rotation of the hand wheel results in the specimen block being moved laterally and upward into position of subsequent sectioning. A stereoemicroscope 45 and lamp 50 are used by the operator to view the sectioning process.

As seen in FIG. 3, diamond knife 30 is held stationary as specimen block 12 is moved down into contact with knife edge 53. Fluid 56 is provided in knife boat 25 such that as each section is cut, it is floated onto the surface of the fluid. The fluid level must, therefore, be high enough in the knife boat to facilitate this process. As seen in FIG. 3, the diamond edge knife 30 has an outer surface 59 which is inclined slightly to the vertical. It is important that surface 59 and specimen block 12 remain dry during the sectioning process to insure that production of sections of uniform thickness.

It has been discovered by the inventor of the present invention that the cause of fluid migration over the knife edge and the resulting unacceptable sectioning of specimens is the buildup of static electric charge on the knife and the specimen block resulting from repeated frictional interaction between these two non-conductors. As successive sections are made, this charge buildup increases until the fluid 56 is attracted sufficiently toward the specimen block 12 as the specimen block 12 approaches the knife to flow over the knife edge 53 and onto knife surface 59. When this occurs, the specimen block will be wetted and proper sectioning will be prevented. Even if wetting does not occur, fluctuation of water level may cause problems with sectioning.

In order to prevent static charge buildup, it has been found advantageous to mount radioactive means 65 in the ultramicrotome. The radioactivity ionizes the air around the specimen block and knife assembly and prevents static electric charge buildup. Pieces of radioactive source material 70 may comprise polonium 210 which radiates principally alpha rays. Alpha rays do not readily penetrate air and, it has been found, the radiation given off by such an arrangement is extremely localized. The specimen block is approximately an inch from the polonium and is irradiated intensively. Where the ultramicrotomist's hand rests on hand wheel 40, however, radiation is at the background level. The polonium used with the present invention is sold as a Static Master 20500 ionizing strip, available from Laboratory Supplies Company, 29 Jeffry Lane, Hicksville, N.Y., 11801. The strips of polonium are lightly plated with gold.

Figure 4:
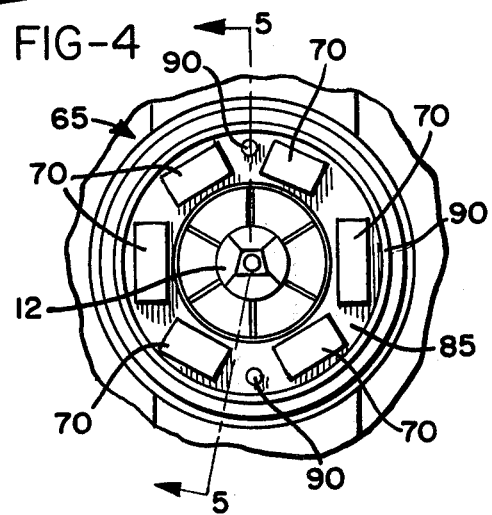
FIG. 4 is an enlarged front view showing the adapter of the present invention, positioned on the ultramicrotome.

Since radioactive polonium 210 emits high intensity alpha radiation, and further since alpha waves do not readily penetrate air, it is necessary that the polonium be positioned very close to the knife and specimen block during sectioning. Although a separate mounting arrangement adjacent the knife and knife boat could be provided for the radioactive material, it has been found advantageous to position the radioactive material around the chuck means which holds the specimen block, as seen in FIGS. 4 and 5.

Figure 5:
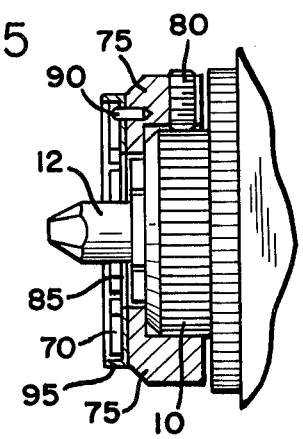
FIG. 5 is a sectional view of the adapter of the present invention, taken generally along FIG. 5—5 in FIG. 4.

As seen in FIG. 5, an adapter ring 75 is provided and is configured to mount on chuck means 10. The adapter ring includes at least one set screw 80 which tightens down onto chuck means 10 and provides firm attachment between the adapter ring 75 and the chuck means 10. Annular mounting means 85 is provided for mounting material 70 around specimen block 12. Material 70 may simply be glued in position on the mounting means 85. Annular mounting means 85 is attached to the adapter ring by snaps 90 which provide for rapid replacement of the radioactive material and annular mounting, without removal or replacement of the adapter ring 75. The annular mounting 85 includes a flange 95 around the periphery of the mount to prevent radioactive material 70 from being touched by the operator of the ultramicrotome when the radioactive material and annular mount are replaced.

It should be understood that various other radioactive materials may be used in place of polonium 210 as a source of alpha rays. Various ones from the following groups may be useful in this regard: radium 226, uranium 238, plutonium 238, plutonium 239, plutonium 240, plutonium 241, uranium 232, neptunium 237, curium 242, americum 241, and thorium 228. All of these isotopes emit strong, ionizing, alpha radiation, very weak gamma radiation, and have relatively long lives.

While the forms of apparatus herein described constitute preferred embodiments of the invention, it is to be understood that the invention is not limited to these precise forms of apparatus, and that changes may be made therein without departing from the scope of the invention.

What is claimed is:

1. An ultramicrotome for preparing sections for electron microscope analysis, comprising:
    chuck means for holding a specimen which is to be sectioned,
    stationary knife assembly means for cutting said specimen, said knife assembly means including a knife boat for holding a quantity of fluid and a knife held by said knife boat, said knife defining one side of said knife boat,
    means for moving said chuck means, and said specimen held thereby, into contact with said knife such that sections are cut from said specimen and floated onto the surface of the fluid held in said knife boat, and
    radioactive means mounted on said ultramicrotome for discharging static electric charge which may have accumulated on said chuck means, the specimen, and said knife assembly means, whereby the static electric attractive force on the fluid held in said knife boat is reduced and the fluid prevented from migrating over said knife as said chuck means approaches said knife.

2. The ultramicrotome of claim 1 in which said radioactive means comprises an adapter ring mounted on said chuck means adjacent the specimen, an annular mount attached to said adapter ring, and radioactive material mounted on said annular mount, whereby said annular mount and the radioactive material mounted thereon may conveniently be replaced without removal of said adapter ring.

3. The ultramicrotome of claim 2 in which said annular mount includes a flange around the periphery of said annular mount to prevent said radioactive material from being touched by the operator of the ultramicrotome.

4. The ultramicrotome of claim 1 in which said radioactive means comprises means for positioning radioactive polonium adjacent the specimen held by said chuck means.

5. The ultramicrotome of claim 4 in which said polonium is $^{210}$Po.

6. The ultramicrotome of claim 1 in which said radioactive means includes a source of alpha rays.

7. An attachment for an ultramicrotome, said ultramicrotome having a chuck means for holding a specimen, a stationary knife assembly with a knife edge cutting the specimen and including a fluid-filled knife boat, and means for moving the chuck means into contact with the knife edge, comprising:
   radioactive source for supplying radiation, and
   adapter means for mounting said radiation source means on said ultramicrotome, whereby the knife assembly and the chuck means are irradiated and accumulation of static electric charge on the chuck means, the specimen, or the knife assembly is prevented.

8. The attachment of claim 7 in which said adapter means comprises:
   an adapter ring, configured to mount on the chuck means and having at least one set screw for attaching the adapter ring to the chuck means, and
   annular mounting means for mounting said radioactive source means, said annular mounting means being attached by at least one snap mechanism to said adaptor ring, whereby said annular mounting means and said radioactive source means may be easily detached from said adapter ring.

9. The attachment of claim 8 in which said radioactive source comprises polonium 210.

10. The attachment means of claim 7 in which said radioactive source comprises a source of alpha rays.

11. The attachment of claim 8 in which said radioactive source comprises thorium 228.

12. The attachment of claim 8 in which said radioactive source comprises an isotope of an element selected from the group consisting of: radium, uranium, thorium, plutonium, americium, curium, and neptunium.

* * * * *